(12) United States Patent
Sweeney

(10) Patent No.: US 9,986,918 B2
(45) Date of Patent: Jun. 5, 2018

(54) SYSTEMS AND METHODS TO INDICATE HEART FAILURE CO-MORBIDITY

(75) Inventor: Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1393 days.

(21) Appl. No.: 13/408,315

(22) Filed: Feb. 29, 2012

(65) Prior Publication Data

US 2012/0238886 A1 Sep. 20, 2012

Related U.S. Application Data

(60) Provisional application No. 61/452,495, filed on Mar. 14, 2011.

(51) Int. Cl.
| | |
|---|---|
| A61B 5/02 | (2006.01) |
| A61B 5/0205 | (2006.01) |
| A61B 5/00 | (2006.01) |
| A61B 5/021 | (2006.01) |
| A61B 5/08 | (2006.01) |
| A61B 5/11 | (2006.01) |

(Continued)

(52) U.S. Cl.
CPC ........ *A61B 5/02055* (2013.01); *A61B 5/0031* (2013.01); *A61B 5/021* (2013.01); *A61B 5/08* (2013.01); *A61B 5/11* (2013.01); *A61B 5/14551* (2013.01); *A61B 5/4836* (2013.01); *A61N 1/3627* (2013.01)

(58) Field of Classification Search
CPC ....................................................... A61B 5/021
See application file for complete search history.

(56) References Cited

U.S. PATENT DOCUMENTS 6,336,903 B1 * 1/2002 Bardy .................. A61B 5/0002
600/508
6,858,006 B2    2/2005 MacCarter et al.
(Continued)

FOREIGN PATENT DOCUMENTS

EP          1709993 A1    10/2006
EP          1151718 B1    1/2007
(Continued)

*Primary Examiner* — Patricia Mallari
*Assistant Examiner* — Vasuda Ramachandran
(74) *Attorney, Agent, or Firm* — Schwegman Lundberg & Woessner, P.A.

(57) ABSTRACT

Systems and methods to indicate heart failure co-morbidity are described. In an example, one or more physiological signals can be analyzed for a specified time period to determine at least one of an indication of a heart failure event or a characteristic of heart failure co-morbidity, such as a characteristic of a non-heart failure physiological event. At least one of the different physiological signals can be compared to a specified criterion indicative of the heart failure event to provide a comparison value, where the comparison value is indicative of whether the at least one of the different physiological signals contributed towards the indication of the heart failure event. An indication of a non-heart failure physiological event can be determined using the heart failure event indication, the non-heart failure physiological event characteristic, and the comparison value indicative of whether the one or more physiological signals contributed towards the heart failure event.

20 Claims, 7 Drawing Sheets

(51) Int. Cl.
    *A61B 5/1455*     (2006.01)
    *A61N 1/362*     (2006.01)

(56) References Cited

U.S. PATENT DOCUMENTS

| | | |
|---|---|---|
| 6,974,413 B2 | 12/2005 | Bardy |
| 6,978,169 B1 | 12/2005 | Guerra |
| 7,024,369 B1 | 4/2006 | Brown et al. |
| 7,115,096 B2 | 10/2006 | Siejko et al. |
| 7,117,028 B2 | 10/2006 | Bardy |
| 7,258,670 B2 | 8/2007 | Bardy |
| 7,299,086 B2 | 11/2007 | McCabe et al. |
| 7,314,451 B2 | 1/2008 | Halperin et al. |
| 7,433,853 B2 | 10/2008 | Brockway et al. |
| 7,577,475 B2 | 8/2009 | Cosentino et al. |
| 7,590,449 B2 | 9/2009 | Mann et al. |
| 7,616,991 B2 | 11/2009 | Mann et al. |
| 7,787,946 B2 | 8/2010 | Stahmann |
| 2004/0122485 A1 | 6/2004 | Stahmann et al. |
| 2006/0155204 A1 | 7/2006 | Wariar et al. |
| 2009/0069708 A1 | 3/2009 | Hatlestad et al. |
| 2010/0094102 A1 | 4/2010 | Zhang et al. |
| 2011/0009753 A1 | 1/2011 | Zhang |

FOREIGN PATENT DOCUMENTS

| | | |
|---|---|---|
| EP | 1151719 B1 | 9/2007 |
| EP | 1177764 B1 | 5/2008 |

\* cited by examiner

| | | | | | | | | |
|---|---|---|---|---|---|---|---|---|
| 712 — HF Event Indication | 0 | 0 | 0 | 0 | 1 | 1 | 1 | 1 |
| 714 — Non-HF Physiological Event Characteristic | 0 | 0 | 1 | 1 | 0 | 0 | 1 | 1 |
| 716 — Comparison Value | 0 | 1 | 0 | 1 | 0 | 1 | 0 | 1 |
| 710 — Non-HF Physiological Event Indication | 0 | 0 | 1 | 1 | 0 | 0 | 1 | 0 |

SYSTEMS AND METHODS TO INDICATE HEART FAILURE CO-MORBIDITY

CLAIM OF PRIORITY

This application claims the benefit of priority under 35 U.S.C. § 119(e) of Sweeney, U.S. Provisional Patent Application Ser. No. 61/452,495, entitled "SYSTEMS AND METHODS TO INDICATE HEART FAILURE CO-MORBIDITY," filed on Mar. 14, 2011, which is herein incorporated by reference in its entirety.

BACKGROUND

Patient monitoring systems can be used to automate the monitoring of a patient's physiological condition. In clinical settings, such as hospitals, such monitoring systems can allow a treating clinician to manage the care of one or more patients more efficiently, such as by providing access to the physiological condition of one or more patients to a clinician from a centralized location. A remote monitoring system can allow a patient to live at home or in an extended-care facility while still allowing close supervision of the patient's physiological condition by the treating clinician.

In Bardy, U.S. Pat. No. 7,117,028, a system for ordering and prioritizing multiple health disorders for automated remote patient care is discussed. The system collects physiological information from a patient over time and changes in patient status are determined by observing differences in the physiological condition over time.

In Brockway, U.S. Pat. No. 7,433,853, a plurality of sensors is used to facilitate diagnosis and medical decision making for an individual patient. An expert system evaluates the sensor data, combines the sensor data with stored probability data, and provides an output signal for notification or medical intervention.

OVERVIEW

Systems and methods to indicate heart failure co-morbidity are described. In an example, one or more physiological signals can be analyzed for a specified time period to determine at least one of an indication of a heart failure event or a characteristic of heart failure co-morbidity, such as a characteristic of a non-heart failure physiological event. At least one of the different physiological signals can be compared to a specified criterion indicative of the heart failure event to provide a comparison value, where the comparison value is indicative of whether the at least one of the different physiological signals contributed towards the indication of the heart failure event. An indication of a non-heart failure physiological event can be determined using the heart failure event indication, the non-heart failure physiological event characteristic, and the comparison value indicative of whether the one or more physiological signals contributed towards the heart failure event.

In an example, a heart failure event indication can be determined from an analysis of different physiological signals associated with the physiological condition of the subject. A non-heart failure physiological event characteristic can be determined using at least one of the different physiological signals. A comparison value can be determined to indicate whether the at least one of the different physiological signals meets the at least one criterion indicative of the heart failure event. A non-heart failure physiological status indication can then be determined, such as by using the heart failure event indication, the non-heart failure event characteristic, and the comparison value.

Example 1 can include subject matter (such as a system, a method, a means for performing acts, or a machine-readable medium including instructions that, when performed by the machine, cause the machine to perform acts, etc.) that can include a heart failure event detection circuit, a non-heart failure physiological event detection circuit, a comparison circuit, and a non-heart failure status indicator circuit. The heart failure event detection circuit can be configured to analyze information from different physiological signals to determine a heart failure event indication corresponding to a time period. The non-heart failure physiological event detection circuit can be configured to determine a non-heart failure physiological event characteristic using at least one of the different physiological signals. The comparison circuit can be configured to compare the at least one of the different physiological signals to a specified criterion indicative of the heart failure event to provide a comparison value indicating whether the at least one of the different physiological signals meets the criterion indicative of the heart failure event. The non-heart failure status indicator circuit can be coupled to the heart failure event detection circuit, the non-heart failure physiological event detection circuit, and the comparison circuit. The non-heart failure status indicator circuit can be configured to compute a non-heart failure physiological status indication using the heart failure event indication, the non-heart failure event characteristic, and the comparison value. The non-heart failure physiological event indication can indicate that the non-heart failure physiological event is absent, during the time period, when (1) the heart failure event indication indicates that the heart failure event is present during the time period, (2) the non-heart failure event characteristic indicates that the non-heart failure physiological event is present during the time period, and (3) the comparison value indicates that at least one of the different physiological signals does meet the criterion indicative of the heart failure event.

In Example 2, the subject matter of Example 1 can optionally be configured such that the non-heart failure physiological event indication can be configured to indicate that the non-heart failure physiological event is present, during the time period, when (1) the heart failure event indication indicates that the heart failure event is present during the time period, (2) the non-heart failure event characteristic indicates that the non-heart failure physiological event is present during the time period, and (3) the comparison value indicates that at least one of the different physiological signals fails to meet the criterion indicative of the heart failure event.

In Example 3, the subject matter of one or any combination of Examples 1-2 can optionally be configured such that the non-heart failure physiological event indication indicates that the non-heart failure physiological event is present, during the time period, when (1) the heart failure event indication indicates that the heart failure event is absent during the time period, (2) the non-heart failure event characteristic indicates that the non-heart failure physiological event is present during the time period, and (3) the comparison value indicates that at least one of the different physiological signals fails to meet the criterion indicative of the heart failure event.

In Example 4, the subject matter of one or any combination of Examples 1-3 can optionally include a sensor configured to provide at least one physiological signal.

In Example 5, the subject matter of one or any combination of Examples 1-4 can optionally be configured such that the sensor is configured to provide at least one of a heart rate signal, a respiration signal, a blood pressure signal, a lung tidal volume signal, a physical activity level signal, a weight signal, a posture signal, an impedance signal (e.g., a thoracic impedance signal), a heart sound signal, an airflow or respiration signal, a blood flow signal (e.g., a blood pressure signal), a minute ventilation signal, an electrocardiogram, a temperature signal, an autonomic tone signal, an autonomic balance signal, a hematocrit signal, a cardiac muscle contractility signal, an oxygen saturation level signal, a blood analyte signal (e.g., a blood gas concentration signal), or a myocardial ischemia signal.

In Example 6, the subject matter of one or any combination of Examples 1-5 can optionally be configured such that the physiological sensor is configured to provide a respiration signal.

In Example 7, the subject matter of one or any combination of Examples 1-6 can optionally include the specified criterion indicative of the heart failure event comprising a threshold, wherein the threshold corresponds to an interaction characteristic of two or more physiological signals.

In Example 8, the subject matter of one or any combination of Examples 1-7 can optionally be configured such that a first physiological signal is a respiration rate having a high respiration rate characteristic, and a second physiological signal is a weight signal having a weight gain characteristic.

In Example 9, the subject matter of one or any combination of Examples 1-8 can optionally be configured such that the specified criterion indicative of the heart failure event is a threshold.

In Example 10, the subject matter of one or any combination of Examples 1-9 can optionally be configured such that the specified criterion indicative of the heart failure event is a weighting factor, wherein the weighting factor corresponds to an interaction characteristic of two or more physiological signals.

In Example 11, the subject matter of one or any combination of Examples 1-10 can optionally include a remote monitoring system communicatively coupled to the heart failure event detection circuit and the non-heart failure status indicator circuit, wherein the remote monitoring system is configured to provide the heart failure event indication and the non-heart failure physiological status indication to a user.

In Example 12, the subject matter of one or any combination of Examples 1-11 can optionally be configured such that the remote monitoring system is configured to provide the heart failure event indication and the non-heart failure physiological event indication to a user through a graphical user interface.

In Example 13, the subject matter of one or any combination of Examples 1-12 can optionally be configured such that the heart failure event indication is a binary value.

In Example 14, the subject matter of one or any combination of Examples 1-13 can optionally be configured such that the heart failure event indication comprises a heart failure event status indication and physiological sensor signal information.

In Example 15, the subject matter of one or any combination of Examples 1-14 can optionally be configured such that the non-heart failure physiological status indication comprises a non-heart failure event status indication and physiological sensor signal information.

Example 16 can include subject matter such as a method that can comprise: analyzing information from different physiological signals by a heart failure event detection circuit to determine a heart failure event indication corresponding to a time period, determining a non-heart failure physiological event characteristic by a non-heart failure physiological event detection circuit using at least one of the different physiological signals, comparing the at least one of the different physiological signals to a specified criterion indicative of the heart failure event to provide a comparison value indicating whether the at least one of the different physiological signals meets the criterion indicative of the heart failure event, and computing a non-heart failure physiological event indication using the heart failure event indication, the non-heart failure event characteristic, and the comparison value. The non-heart failure physiological event indication can indicate that the non-heart failure physiological event is absent, during the time period, when (1) the heart failure event indication indicates that the heart failure event is present during the time period, (2) the non-heart failure event characteristic indicates that the non-heart failure physiological event is present during the time period, and (3) the comparison value indicates that at least one of the different physiological signals does meet the criterion indicative of the heart failure event.

In Example 17, the subject matter of Example 16 can optionally include indicating that the non-heart failure physiological event is present, during the time period, when (1) the heart failure event indication indicates that the heart failure event is present during the time period, (2) the non-heart failure event characteristic indicates that the non-heart failure physiological event is present during the time period, and (3) the comparison value indicates that at least one of the different physiological signals fails to meet the criterion indicative of the heart failure event.

In Example 18, the subject matter of one or any combination of Examples 16 or 17 can optionally include indicating that the non-heart failure physiological event is present, during the time period, when (1) the heart failure event indication indicates that the heart failure event is absent during the time period, (2) the non-heart failure event characteristic indicates that the non-heart failure physiological event is present during the time period, and (3) the comparison value indicates that at least one of the different physiological signals fails to meet the criterion indicative of the heart failure event.

In Example 19, the subject matter of one or any combination of Examples 16-18 can optionally include receiving at least one physiological sensor signal from a sensor.

In Example 20, the subject matter of one or any combination of Examples 16-19 can optionally include receiving, using a physiological sensor, at least one of a heart rate signal, a respiration signal, a blood pressure signal, a lung tidal volume signal, a physical activity level signal, a weight signal, a posture signal, an impedance signal (e.g., a thoracic impedance signal), a heart sound signal, an airflow or respiration signal, a blood flow signal (e.g., a blood pressure signal), a minute ventilation signal, an electrocardiogram, a temperature signal, an autonomic tone signal, an autonomic balance signal, a hematocrit signal, a cardiac muscle contractility signal, an oxygen saturation level signal, a blood analyte signal (e.g., a blood gas concentration signal), or a myocardial ischemia signal.

In Example 21, the subject matter of one or any combination of Examples 16-20 can optionally include providing a respiration signal using a physiological sensor.

In Example 22, the subject matter of one or any combination of Examples 16-21 can optionally include a first physiological signal comprising a respiration rate having a high respiration rate characteristic and a second physiological signal comprising a weight signal having a weight gain characteristic.

In Example 23, the subject matter of one or any combination of Examples 16-22 can optionally include a specified criterion indicative of a heart failure event, comprising a specified criterion as a threshold.

In Example 24, the subject matter of one or any combination of Examples 16-23 can optionally include communicating a heart failure event indication and a non-heart failure physiological status indication to a user through a remote monitoring system communicatively coupled to a heart failure event detection circuit and a non-heart failure status indicator circuit.

In Example 25, the subject matter of one or any combination of Examples 16-24 can optionally include providing a heart failure event indication and a non-heart failure physiological event indication to a user through a graphical user interface.

In Example 26, the subject matter of one or any combination of Examples 16-25 can optionally include a heart failure event indication comprising a binary value.

In Example 27, the subject matter of one or any combination of Examples 16-26 can optionally include a heart failure event indication comprising a heart failure event status indication and physiological sensor signal information.

In Example 28, the subject matter of one or any combination of Examples 16-27 can optionally include a non-heart failure physiological status indication comprising a non-heart failure event status indication and physiological sensor signal information.

Example 29 can include subject matter (such as an apparatus, a method, a means for performing acts, or a machine-readable medium including instructions that, when performed by the machine, cause the machine to perform acts) that can include a heart failure event detection circuit, configured to analyze information from different physiological signals to determine a heart failure event indication corresponding to a time period, a non-heart failure physiological event detection circuit, configured to determine a non-heart failure physiological event characteristic using at least one of the different physiological signals, a comparison circuit, configured to compare the at least one of the different physiological signals to a specified first criterion indicative of the heart failure event to provide a comparison value indicating whether the at least one of the different physiological signals meets the criterion indicative of the heart failure event, and a non-heart failure status indicator circuit, coupled to the heart failure event detection circuit and the non-heart failure physiological event detection circuit and the comparison circuit. The non-heart failure status indicator circuit can be configured to compute a non-heart failure physiological status indication using the heart failure event indication, the non-heart failure event characteristic, and the comparison value, wherein the non-heart failure physiological event indication indicates that the non-heart failure physiological event is present, during the time period, when (1) the heart failure event indication indicates that the heart failure event is present during the time period, (2) the non-heart failure event characteristic indicates that the non-heart failure physiological event is present during the time period, (3) and the comparison value indicates that at least one of the different physiological signals fails to meet the criterion indicative of the heart failure event.

In Example 30, the subject matter of Example 29 can optionally be configured such that the non-heart failure physiological event indication indicates that the non-heart failure physiological event is absent, during the time period, when (1) the heart failure event indication indicates that the heart failure event is present during the time period, (2) the non-heart failure event characteristic indicates that the non-heart failure physiological event is present during the time period, and (3) the comparison value indicates that at least one of the different physiological signals does meet the criterion indicative of the heart failure event.

In Example 31, the subject matter of one or any combination of Examples 29-30 can optionally be configured such that the non-heart failure physiological event indication indicates that the non-heart failure physiological event is present, during the time period, when (1) the heart failure event indication indicates that the heart failure event is absent during the time period, (2) the non-heart failure event characteristic indicates that the non-heart failure physiological event is present during the time period, and (3) the comparison value indicates that at least one of the different physiological signals fails to meet the criterion indicative of the heart failure event.

In Example 32, the subject matter of one or any combination of Examples 29-31 can optionally be configured to include a sensor configured to provide at least one physiological signal.

In Example 33, the subject matter of one or any combination of Examples 29-32 can optionally be configured such that the sensor is configured to provide at least one of a heart rate signal, a respiration signal, a blood pressure signal, a lung tidal volume signal, a physical activity level signal, a weight signal, a posture signal, an impedance signal (e.g., a thoracic impedance signal), a heart sound signal, an airflow or respiration signal, a blood flow signal (e.g., a blood pressure signal), a minute ventilation signal, an electrocardiogram, a temperature signal, an autonomic tone signal, an autonomic balance signal, a hematocrit signal, a cardiac muscle contractility signal, an oxygen saturation level signal, a blood analyte signal (e.g., a blood gas concentration signal), or a myocardial ischemia signal.

In Example 34, the subject matter of one or any combination of Examples 29-33 can optionally be configured such that the physiological sensor is configured to provide a respiration signal.

In Example 35, the subject matter of one or any combination of Examples 29-34 can optionally be configured such that the first physiological signal is a respiration rate having a respiration rate characteristic and the second physiological signal is a temperature signal having a temperature change characteristic.

In Example 36, the subject matter of one or any combination of Examples 29-35 can optionally be configured such that the specified criterion indicative of the heart failure event is a threshold.

In Example 37, the subject matter of one or any combination of Examples 29-36 can optionally be configured such that the specified criterion indicative of the heart failure event is a weighting factor, and the weighting factor corresponds to an interaction characteristic of two or more physiological signals.

In Example 38, the subject matter of one or any combination of Examples 29-37 can optionally to include a remote monitoring system communicatively coupled to the heart failure event detection circuit and the non-heart failure status indicator circuit, wherein the remote monitoring system is configured to provide the heart failure event indication and the non-heart failure physiological status indication to a user.

In Example 39, the subject matter of one or any combination of Examples 29-38 can optionally be configured such that a remote monitoring system is configured to provide the heart failure event indication and the non-heart failure physiological event indication to a user through a graphical user interface.

In Example 40, the subject matter of one or any combination of Examples 29-39 can optionally be configured such that the heart failure event indication comprises a heart failure event status indication and physiological sensor signal information.

In Example 41, the subject matter of one or any combination of Examples 29-40 can optionally be configured such that the non-heart failure physiological status indication comprises a non-heart failure event status indication and physiological sensor signal information.

These examples can be combined in any permutation or combination. This overview is intended to provide an overview of subject matter of present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
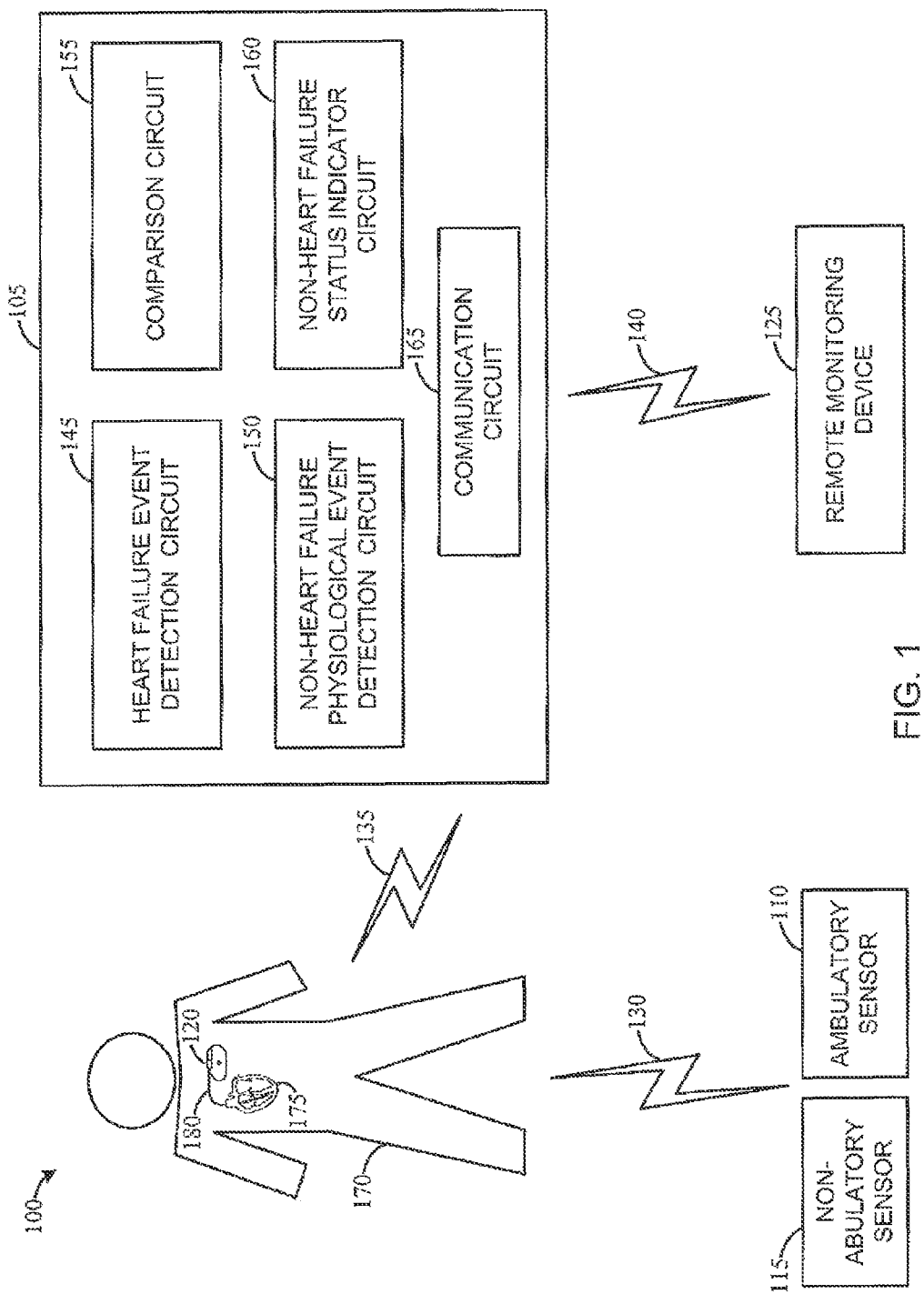
FIG. 1 shows an example of a system to provide a non-heart failure physiological event indication of at least one physiological event that did not contribute to an indication of a heart failure event.

FIG. 1 shows an example of portions of a system 100 that can be configured to detect an indication of at least one physiological event, such as a congestive heart failure ("CHF" or "HF") event, and that can also be configured to provide an indication of a non-heart failure physiological event (e.g., heart failure co-morbidity), where the non-heart failure physiological event was determined not to have contributed towards the indication of the HF event. In au example, the system 100 can include an ambulatory or non-ambulatory medical device, such as a local monitoring device 105 that can be configured to provide an indication of a HF event, a non-HF physiological event, or both. The local monitoring device 105 can be configured to communicate with at least one of an ambulatory sensor 110, a non-ambulatory sensor 115, an implantable medical device (IMD) 120, or a remote monitoring device 125, such as using a communication link 130-140 (e.g., a communication or communication network, a telemetry link, an RF link, a direct wired connection, etc.).

In an example, the local monitoring device 105 can include a communication circuit 165, such as to permit wired or wireless communication with an external device, such as the remote monitoring device 135, ambulatory sensor 110, non-ambulatory sensor 115, or IMD 120 using a communications link 130-140. In an example, the communications link 130-140 can include a communications or computer network, a direct wired connection, an inductive communication link, a radio-frequency (RF) link, or any combination.

In an example, the remote monitoring device 125 can be located remotely (e.g., at a clinic, hospital, caretaker's office, etc.) such as to provide an audible or visual indication of the HF event and the non-HF event indications associated with the subject 170, such as using a graphical user interface (GUI).

The example of the local monitoring device 105 can include a HF event detection circuit 145, a non-HF physiological event detection circuit 150, a comparison circuit 155, a non-HF status indicator circuit 160, and a communication circuit 165. In an example, the IMD 120 can be configured to be implantable in a subject, such as subject 170, such as to provide a therapy to a heart 175 via one or more leads 180, to monitor the physiological condition of the subject, or both.

In an example, the subject 170 can suffer from a primary physiological disorder, such as heart failure, and one or more co-morbidities, (e.g., pneumonia). The subject's caregiver can configure a monitoring device (e.g., the local monitoring device 105, or the remote monitoring device 125) to monitor the subject's physiological condition, such to detect one or more physiological events (e.g., a worsening heart failure event, or an onset of an illness), or to monitor an existing physiological condition. To monitor the subject's physiological condition, the monitoring device 105, 125 can be configured to gather physiological information from one or more sensing sources associated with the subject 170 (e.g., the ambulatory sensor 110, the non-ambulatory sensor 115, the IMD 120, etc.). In an example, the sensing sources can be configured to provide one or more physiological signals (e.g., a weight signal, or a thoracic impedance signal) useful in determining the physiological condition of the subject 170.

In an example, the non-ambulatory sensor 115 can include a scale, a blood analyte (e.g., gas concentration) sensor, or a respiratory sensor device such as having an airflow sensor. Examples of the ambulatory sensor 110 can include a heart sound sensor, a physical activity sensor such as a accelerometer, a cardiac impedance sensor, a posture sensor, an acoustic sensor (e.g., microphone), a respiration sensor, a transthoracic impedance sensor, a pressure sensor, an electrical activity sensor (e.g., an electrocardiogram sensor), or an external respiratory band sensor such as having a piezoelectric or other sensor element. Examples of physiological signals returned by the sensors 110, 115 can include, among others, a heart rate signal, a respiration signal, a blood pressure signal, a lung tidal volume signal, a physical activity level signal, a weight signal, a posture signal, an impedance signal (e.g., a thoracic impedance signal), a heart sound signal, an airflow or respiration signal, a blood flow signal (e.g., a blood pressure signal), a minute ventilation signal, an electrocardiogram, a temperature signal, an autonomic tone signal, an autonomic balance signal, a hematocrit signal, a cardiac muscle contractility signal, an oxygen saturation level signal, a blood analyte signal (e.g., a blood gas concentration signal), or a myocardial ischemia signal.

In an example, the IMD 120 can be configured to deliver a therapy (e.g., bradycardia pacing, anti-tachyarrhythmia pacing (ATP), cardiac contractility modulation (CCM) therapy, cardiac resynchronization therapy (CRT), or atrial or ventricular defibrillation shock therapy) to the heart 175, such as via electrodes that can be located on the implantable lead 180 or elsewhere. In an example, these or other electrodes can be used to provide any of the above-mentioned examples of physiological signals corresponding to the physiological condition of the subject. The electronics unit of the IMD 120 can include one or more components that can be enclosed in a hermetically-sealed canister or "can." In an example, the lead 180 can include one or more intravascular, epicardial, or other leads, such as one or more atrial leads, ventricular leads, or one or more intracardiac vasculature (e.g., coronary sinus) leads. Individual leads can include one or more electrodes. Other electrodes can be located on the can, or on an insulating header extending from the can, or on or coupled to one or more other portions of the IMD 120, such as for one or any combination of pacing, sensing, resynchronization, neurostimulation, cardioversion/defibrillation, impedance monitoring, etc.

A heart sound sensor can be implanted (e.g., in the IMD 120), or used externally, such as to measure the heart sounds associated with mechanical vibrations resulting from heart activity and the flow of blood through the heart 175. Heart sounds within a particular cardiac cycle can be referred to by the associated activity. The first heart sound (S1) is associated with the vibrational sound made by the heart during tensing of the mitral valve. The second heart sound (S2) is associated with the beginning of diastole. The third (S3) and the fourth heart sound (S4) are associated with filling pressures of the left ventricle during diastole. A heart sounds sensor can produce an electrical signal that is representative of mechanical activity of a patient's heart. For example, a single heart sounds sensor can provide an indication of a change in regional shortening of the heart wall, an increase in filling pressure, or an increase in heart chamber contractility.

The heart sounds sensor can be used to detect increased filling pressure of the heart. An increase in S3 heart sound intensity can be an indication of elevated filling pressure of the heart and can be indicative of certain pathological conditions of the heart, including HF. An example of systems and methods that can use an index derived from the S3 heart sound to detect HF are described in commonly assigned U.S. Pat. No. 7,115,096, entitled "Third Heart Sound Activity Index for Heart Failure Monitoring," which is incorporated herein by reference in its entirety, including its description of detecting and using heart sounds to diagnose HF status. An increase in filling pressure (e.g., an increase over many cardiac cycles, of a measure taken during or over a particular cardiac cycle) of the heart can be detected using a pressure sensor, such as a right ventricle chamber pressure sensor, a pulmonary artery pressure sensor, or a left atrial chamber pressure sensor. In some subjects, the increase in filling pressure of the heart can be followed by one or more abnormalities in a subject's electrocardiogram. An example of such abnormality that can follow an increase in filling pressure is having an S-wave to T-wave ("ST") interval of the ECG that is elevated, such as by at least a specified amount from an ST interval of a baseline ECG. An ECG can be sensed using surface (e.g., skin contact) ECG electrodes, using implantable electrodes or can be acquired wirelessly, such as using a wireless ECG sensing circuit to sense a wireless ECG approximating the surface ECG acquired without using skin contact electrodes. An example of a wireless ECG sensing circuit is described in the commonly assigned U.S. Pat. No. 7,299,086, entitled "Wireless ECG in Implantable Devices," which is incorporated herein by reference, including its description of a wireless ECG.

Fluid accumulation can be identified through a weight measurement, decreased thoracic impedance, or both. In an example, the non-ambulatory sensor 115 can include an electronic scale, which can be configured to communicate wirelessly to the IMD 120 or the local monitoring device 105, such as using the communication link 135. Thoracic impedance can be used to measure an accumulation of fluid within the subject 170, for example fluid around the heart or in or around the lungs. In an example, an implanted impedance sensor can provide a high frequency, low amplitude AC signal, such as to measure the resistance between electrodes implanted within the subject 170. An external transthoracic impedance sensor can be used, similarly, to measure thoracic impedance using electrodes, such as can be applied to the subject's skin. Because an applied electrical current encounters less resistance in wetter tissue, a decrease in thoracic impedance (e.g., at frequencies substantially below that of breathing or heart contractions) can correlate to an accumulation of fluid in the thorax. An example of systems and methods that can be used for monitoring pulmonary edema or other thoracic fluid status in a subject using thoracic impedance information are described in commonly assigned U.S. Patent Application Publication No. 2009/0069708 entitled "Histogram-Based Thoracic Impedance Monitoring," which is incorporated herein by reference in its entirety, including its description of using thoracic impedance histogram information to compute and provide a lung fluid status indication.

Generally, HF can be compensated or decompensated. In compensated HF, the subject's condition is stable and the subject's bodily systems can compensate for the reduced cardiac output, such as by increasing the heart rate or increasing stroke volume. In decompensated HF, the subject's systems can no longer compensate for the reduced cardiac output and the subject's organs and tissues no longer receive enough blood flow to function properly. Decompensated HF can be characterized by symptoms such as tachycardia, dyspnea, edema, or irregular heart sounds.

Respiration characteristics of the subject (e.g., dyspnea at rest, dyspnea during physical exertion, elevated respiration rate, etc.) can be indicative of worsening HF. In chronic compensated state, a heart failure patient can have an elevated respiration rate. Shortly before a decompensation episode, the heart failure patient's respiration rate can become more elevated, even at rest. One or more sensors 110-120 can transmit to the IMD 120 or to the local monitoring device 105 one or more respiration signals that can indicate one or more respiration characteristics of the subject 170. Examples of respiration characteristics can include respiration rate, minute ventilation, and tidal volume. The sensors 110-120 can include a variety of sensors, such as an implantable thoracic impedance sensor, an external respiratory band, a respiratory mask flow sensor, or another type of respiration sensor. Examples of techniques that can provide a clinician with a quantifiable respiration characteristic to monitor a patient's changing heart failure status are described in commonly assigned, U.S. patent application Ser. No. 12/787,777, entitled "Respiration Rate Trending for Detecting Early Onset of Worsening Heart Failure," which is incorporated herein by reference, including its description of using a respiration characteristic to monitor heart failure status.

In an example, the HF event detection circuit 145 and the non-HF physiological event detection circuit 150 can be configured to receive one or more physiological signals (e.g., a weight signal received from a scale, a respiration signal received from a respiration sensor, or other physiological signals, such as listed above) corresponding to a physiological condition of the subject 170 at a specified time or within a specified time period, such as through the communication link 130-135. The HF event detection circuit 145 can then analyze information from different physiological signals, (e.g., a respiration rate, a weight change, etc.) to determine a heart failure event indication corresponding to a time period. In an example, the HF event indication can be determined by analyzing the physiological sensor information using a specified criterion, such as a threshold. In an example, the HF event indication can be determined by combining the physiological sensor information using one or more weighting factors prior to testing against a criterion. An example of the criterion is described in greater detail below, such as in reference to the thresholds of FIG. 8. In an example, a HF event detection circuit 145 can be configured to analyze one or more physiological signals to indicate whether a HF event is present. For example, HF event detection circuit can receive a respiration signal and a weight signal from one or more ambulatory sensors 110, 120, respectively. The respiration signal can include information concerning the respiration rate of the subject 170, and the weight signal can include information concerning a weight change of the subject 170.

In an example, the HF event indication can be determined by analyzing information from a single physiological signal, such as just analyzing a respiration rate or just analyzing a weight change. For example, the HF event indication can be configured to indicate that a HF event is present if either the respiration rate information meets or exceeds a specified threshold (e.g., respiration rate value is greater than or equal to a first threshold, the respiration rate value is less than a second threshold, etc.). In an example, the I-IF event indication can be determined by combining two or more physiological signals into a composite signal, which can then be tested against at least one criterion.

In an example, the non-HF physiological event detection circuit 150 can be configured to analyze physiological signal information (e.g., a weight change, a respiration rate, a blood oxygen level, a thoracic impedance value, etc), received from the above mentioned signals to determine a characteristic of a non-HF physiological event. The physiological signal information can be analyzed individually, or in any combination, such as to determine the characteristic of a non-HF physiological event, using a criterion such as a specified fixed threshold, a weighting factor, or a specified threshold that varies, such as varying as a function of information associated with one or more of the physiological signals. In an example, a characteristic of a non-HF physiological event can be determined from information from a single physiological signal, such as a weight signal (e.g., weight loss greater than a specified threshold occurring within a specified time can be characteristic of an overdiuresis condition). In an example, the non-HF physiological event characteristic can be determined from a combination of signals, such as, a respiration signal and a temperature signal (e.g., a respiration rate greater than a first threshold combined with an internal body temperature increase greater than a second threshold can be characteristic of pneumonia).

In an example, the comparison circuit 155 can be configured to determine a comparison value (e.g., a variable) representative of whether a physiological signal or a combination of physiological signals, contributed towards an indication of a HF event. The comparison value can be used to determine whether a non-HF physiological event is to be indicated, such as by the non-HF physiological status indicator circuit 160. In an example, the comparison circuit 155 can compare a signal, or combination of signals, such as combined using one or more weighting factors, to a specified criterion (e.g., a threshold, a function of signals, a weighting factor, etc.) where the comparison results in a binary value indicative of whether the signal contributed to a HF event indication, either alone or in combination with other signals (e.g., yes the signal did contribute, no the signal did not contribute). The criterion can be the same as or different from a criterion used by the HF event detection circuit 145, or can vary as a function of one or more of the signals. For example, the comparison circuit 155 can be configured to analyze at least one of a respiration signal, a weight signal, or a temperature signal. The comparison circuit 155 can specify a comparison value associated with the signal or combination of signals analyzed. In an example, the comparison circuit 155 can determine a comparison value that indicates that a weight signal individually contributed to the HF event indication (e.g., a weight above a specified threshold) or did not contribute to the HF event indication (e.g., a weight loss, or a weight gain less than a threshold). In an example, the comparison value can indicate that the weight signal in combination with one or more other physiological signals contributed to a HF event indication by using a second criterion.

In an example, the non-HF physiological status indicator circuit 160 can be configured to provide an indication of whether a non-HF physiological event is present, such as using the HF indication of the HF event detection circuit 145, the non-HF physiological event characteristic from the non-HF physiological event detection circuit 150, and the comparison value of the comparison circuit 155. In an example, the non-HF physiological event indicator circuit 160 can indicate that the non-HF physiological event is present during a time period when (1) the HF event indication indicates that the BF event is present, (2) the non-heart failure event characteristic indicates that the non-HF physiological event is present, and (3) the comparison value indicates that the physiological signal indicative of the non-HF physiological event failed to meet the at least one criterion indicative of the heart failure event. For example, a respiration rate signal indicative of an increased respiration rate can be indicative of a HF event. However, an elevated respiration rate combined with a temperature signal corresponding to an elevated internal body temperature can indicate a non-HF physiological event characteristic of an illness (e.g., pneumonia). In such a case, non-HF status indicator circuit 160 can indicate that a non-HF physiological event condition is present when a HF event is indicated as being present.

In an example, the non-HF physiological status indicator circuit 160 can indicate whether a non-HF physiological event is present or absent. In an example, the non-HF physiological status indicator circuit 160 can be configured to mask the indication of a non-HF physiological event (e.g., indicate the non-HF physiological event as being absent) when the non-HF physiological event contributed to a HF status indication. In an example, the non-HF physiological status indicator circuit 160 can indicate that the non-HF physiological event is absent during a time period when (1) the heart failure event indication indicates that the heart failure event is present during the time period (e.g., a respiration signal, a weight signal, or a thoracic impedance signal indicate a HF condition), (2) the non-heart failure event characteristic indicates that the non-heart failure physiological event is present during the time period (e.g., the respiration signal indicates a rapid respiration rate), and the (3) comparison value indicates that at least one of the different physiological signals does meet the at least one criterion indicative of the heart failure event. An example of the operation of the non-HF physiological status indicator circuit 160 is described in more detail below with the description of the truth table of FIG. 7.

Because the system 100 can include processing capability within the local monitoring device 105, ambulatory sensor 110, non-ambulatory sensor 115, IMD 120, or remote monitoring device 125, various functions or methods discussed in this document can be implemented at any of such locations, such as using an application-specific integrated circuit (ASIC) constructed to perform one or more particular functions, or a general-purpose circuit programmed to perform such functions. Such a general-purpose circuit can include a microprocessor, a microcontroller, or a programmable logic circuit, or a portion of one or more of these. In an example, the tasks of such functions or methods can be distributed between two or more of such locations.

Figure 2:
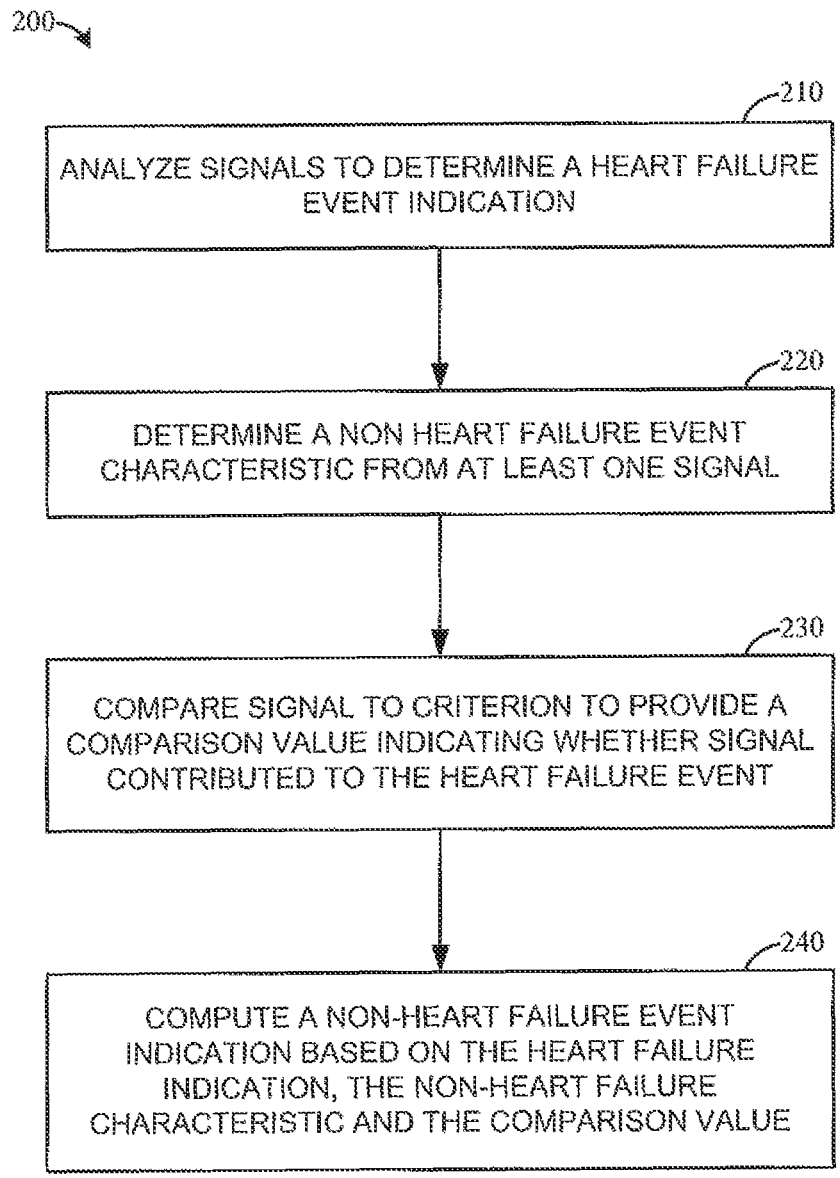
FIG. 2 shows an example of a method to provide a non-heart failure physiological event indication of at least one physiological event that did not contribute to an indication of a heart failure event.

FIG. 2 shows an example of a method 200 to provide a non-heart failure physiological event indication of at least one physiological event that did not contribute to an indication of a heart failure event. For example, the method 200 can provide an indication of a heart failure event or a non-heart failure physiological event, such as can be provided by the local monitoring device 105. At 210, different (e.g., two or more) physiological signals, such as obtained from a sensor 110-120, can be analyzed to determine a HF event indication that can indicate whether a heart failure event is present, such as by using the HF event detection circuit 145. In an example, this can include comparing one or more of the physiological signals to compare one or more physiological signals to at least one criterion, such as a threshold, where the criterion can be pre-defined, can include applying one or more rules, or can vary as a function of one or more of the physiological signals. In an example, the HF event indication can be determined by detecting a physiological change event from a signal sensor and determining whether the detected physiological change event can indicate a heart failure event, such as described in the commonly assigned U.S. patent application Ser. No. 12/576,453, entitled "Multi-sensor Strategy for Heart Failure Patient Management," which is incorporated in its entirety, including its description of declaring whether a change in HF status has occurred using a first and second rule.

At 220, for example, a non-HF physiological event characteristic can be determined using one or more physiological signals, alone or in any combination, such as by using the non-HF physiological event detection circuit 150. In an example, the non-HF physiological event characteristic can be determined for the one or more different physiological signals using at least one criterion, such as a specified threshold. In an example, the one or more physiological signals corresponding to a specified time or specified time period can be compared to the specified threshold. If the examined one or more physiological signals satisfy the criterion, then the non-HF physiological event characteristic can be indicated as being present, otherwise the non-HF physiological event characteristic can be indicated as absent.

At 230, one or more of the physiological signals can be compared to at least one criterion, such as to determine a comparison value indicating whether the signal or a combination of signals contributed towards a HF event indication, such as by using a comparison circuit 155. The criterion can be the same as, or different than the criterion used in determining the HF event indication or the non-HF physiological event characteristic. In an example, the comparison circuit 155 can be incorporated into another circuit, such as the HF event detection circuit 145, where, for example, the comparison value can be generated during the determination of the HF event indication.

At 240, non-HF physiological event indication can be determined based on the HF indication, the non-HF physiological event characteristic, and the comparison value, such as to indicate whether the non-HF physiological event is present or absent. In an example, the non-HF physiological event can be masked, or otherwise indicated as being absent, when the physiological event has contributed towards a HF event indication. In an example, the non-HF physiological event indication can be determined using at least one criterion, such as the truth table of FIG. 7.

Figure 3:
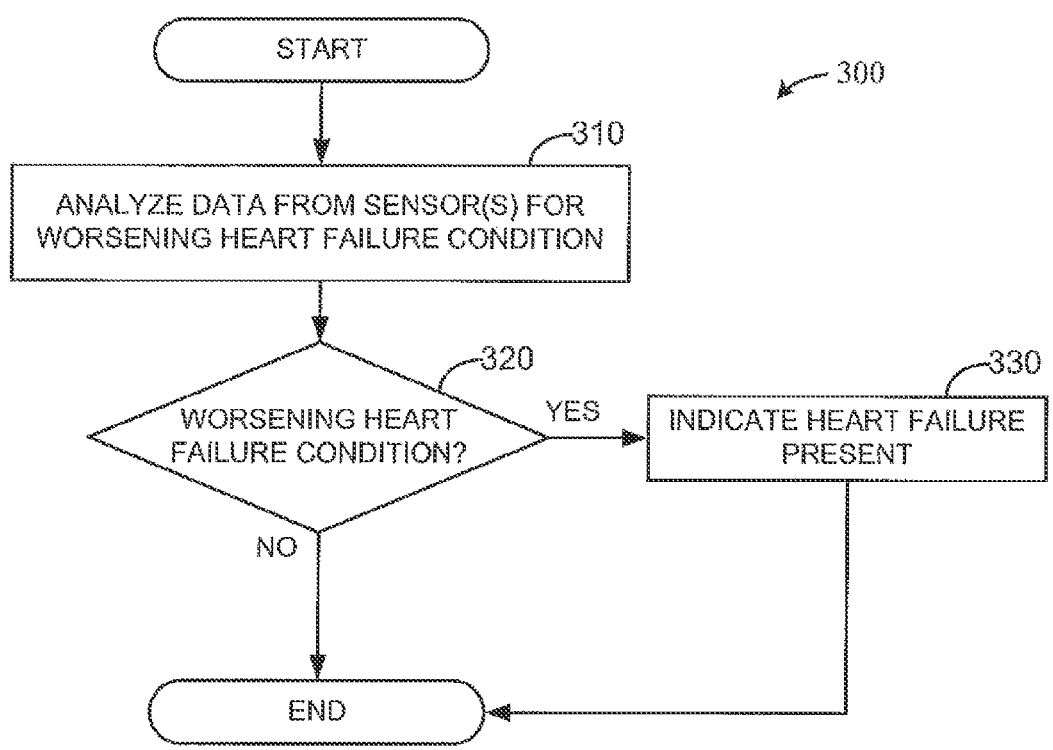
FIG. 3 illustrates an example of a portion of a method to provide a non-heart failure physiological event indication of at least one physiological event that did not contribute to an indication of a heart failure event.

FIG. 3 illustrates an example of a portion of the method of FIG. 2 to provide a non-heart failure physiological event indication of at least one physiological event that did not contribute to an indication of a heart failure event. At 310, physiological data received from a physiological sensor signal can be analyzed to determine a HF event indication, such as by analyzing different physiological signals in the HF event detection circuit 145. At 320, the HF event detection circuit 145 can determine whether the HF event was detected. If so, the HF event indication indicates that the HF event is present at 330 and the illustrated process exits. Otherwise, the illustrated process exits.

Figure 4:
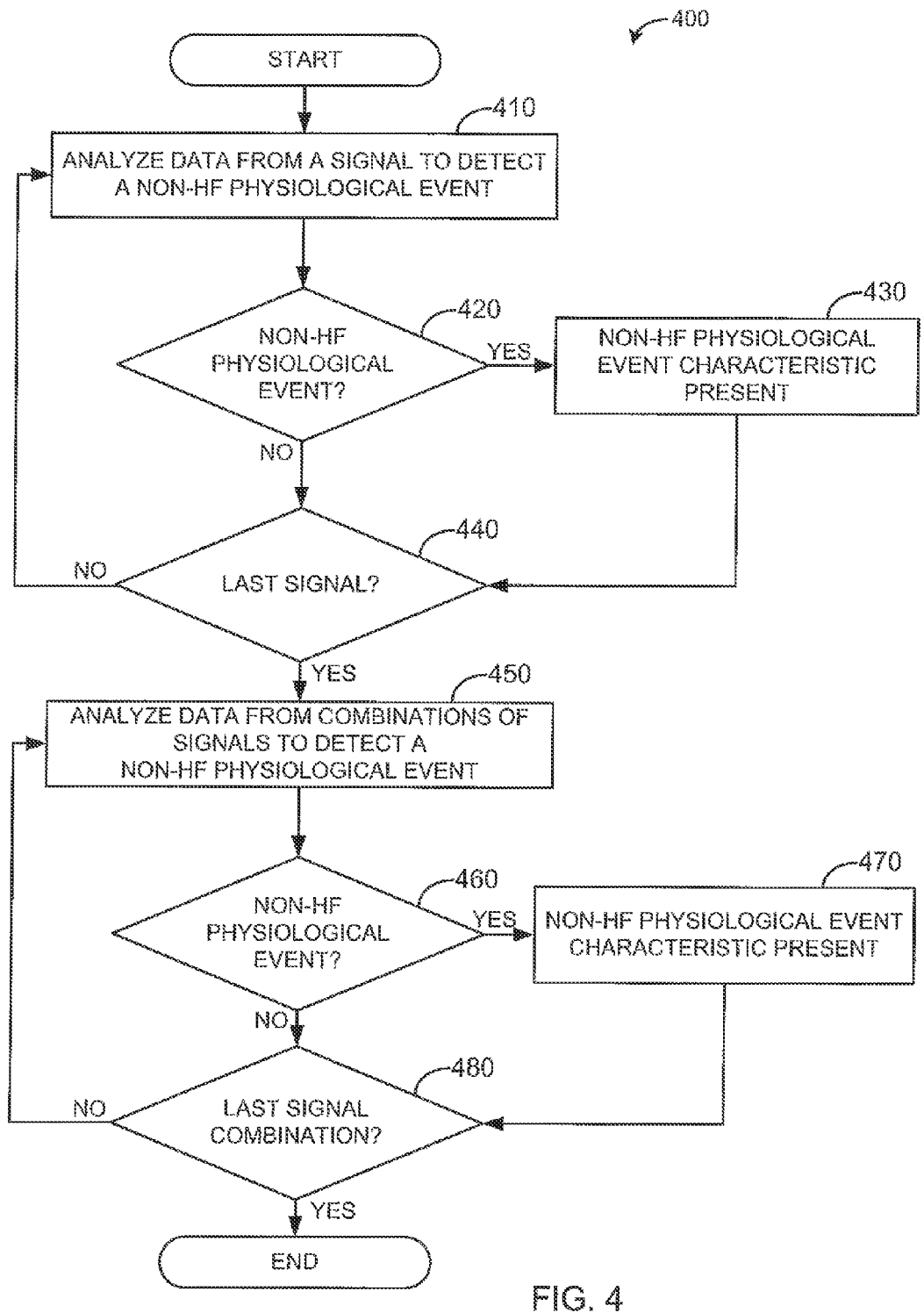
FIG. 4 shows an example of a portion of a method to provide a non-heart failure physiological event indication of at least one physiological event that did not contribute to an indication of a heart failure event.

FIG. 4 shows an example of a portion of a method 400 to provide a non-heart failure physiological event indication of at least one physiological event that did not contribute to an indication of a heart failure event. For example, the method 400 can provide a non-HF physiological event characteristic, such as described above at 220 of FIG. 2. At 410, a local monitoring device 105, such as by the non-HF physiological event detection circuit 150, can analyze a physiological sensor signal associated with the subject 170, such as by using a threshold, to determine, whether the non-HF physiological event is present. At 420, if a non-HF physiological event detection circuit 150 detects a characteristic of the non-HF physiological event, the characteristic of a non-HF physiological event is marked as being present at 430 and flow continues to 440. Returning to 420, if no characteristic of a non-HF physiological event was detected, the non-HF physiological event detection circuit 150 determines whether the last physiological signal (e.g., the last signal of the one or more physiological sensor signals received by the local monitoring device 105) was individually analyzed at 440. If other physiological signals are to be analyzed, the non-HF physiological event detection circuit analyzes the next signal at 410. Otherwise, at 450, different combinations of physiological signals (e.g., (1) a weight signal, a respiration rate signal, and a thoracic impedance signal, or (2) a respiration rate signal and a temperature signal) can be analyzed to determine whether the combination of signals are representative of a characteristic of a non-HF physiological event. At 460, if the combination of signals is indicative of a non-HF physiological event characteristic, the non-HF physiological event detection circuit 150 can indicate that the characteristic of a non-HF physiological event is present at 470 before determining whether the last combination of signals has been analyzed at 480. Returning to 460, if no characteristic of a non-HF physiological event is indicated by the analysis, the non-HF physiological event detection circuit 150 can determine whether the last combination of signals have been analyzed at 480. If the last combination of physiological signals has been analyzed, the illustrated process exits, otherwise the next physiological signal combination can be analyzed at 450.

Figure 5:
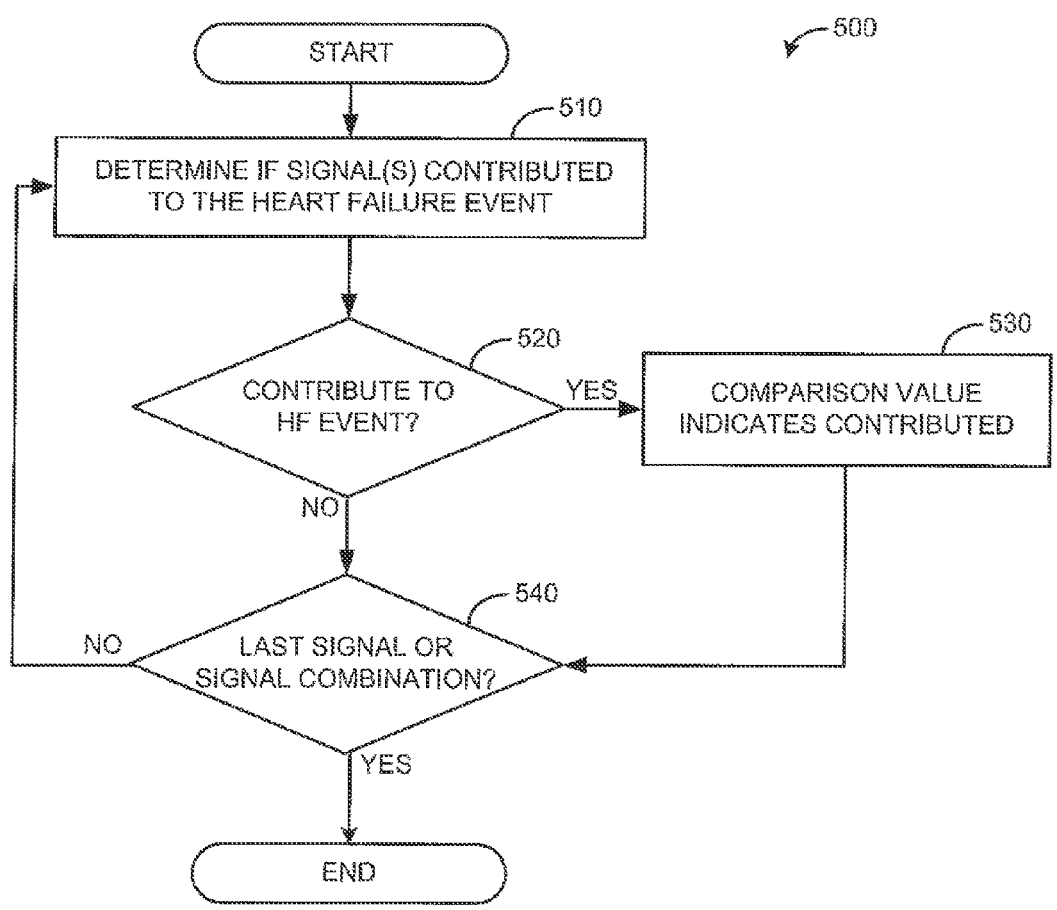
FIG. 5 shows an example of a portion of a method to provide a non-heart failure physiological event indication of at least one physiological event that did not contribute to an indication of a heart failure event.

FIG. 5 shows an example of a portion of a method 500 to provide a non-heart failure physiological event indication of at least one physiological event that did not contribute to an indication of a heart failure event. For example, the method 500 can compare different physiological signals, such as an individual signal or a combination of signals, to at least one criterion, such as a threshold, such as to determine a comparison value indicative of whether a physiological signal or combination of physiological signals contributed towards a HF event indication. At 510, a physiological signal (e.g., a weight signal), or combination of physiological signals (e.g., a weight signal and a respiration rate signal) can be analyzed, such as by comparison circuit 155, such as to determine whether the signal contributed towards a HF event indication, such as by comparing the signal or signals to a threshold. If, at 520, the comparison circuit 155 determines that the signal or combination of signals met the criterion, the comparison circuit 155 can indicate that the criterion has been met, such as by using a threshold at 530, and flow continues to 540. If not, the comparison circuit 155 can determine whether the last signal or combination of signals has been analyzed at 540. If so, the method ends, otherwise to the comparison circuit 155 can return to 510 to analyze the next signal or combination of signals.

Figure 6:
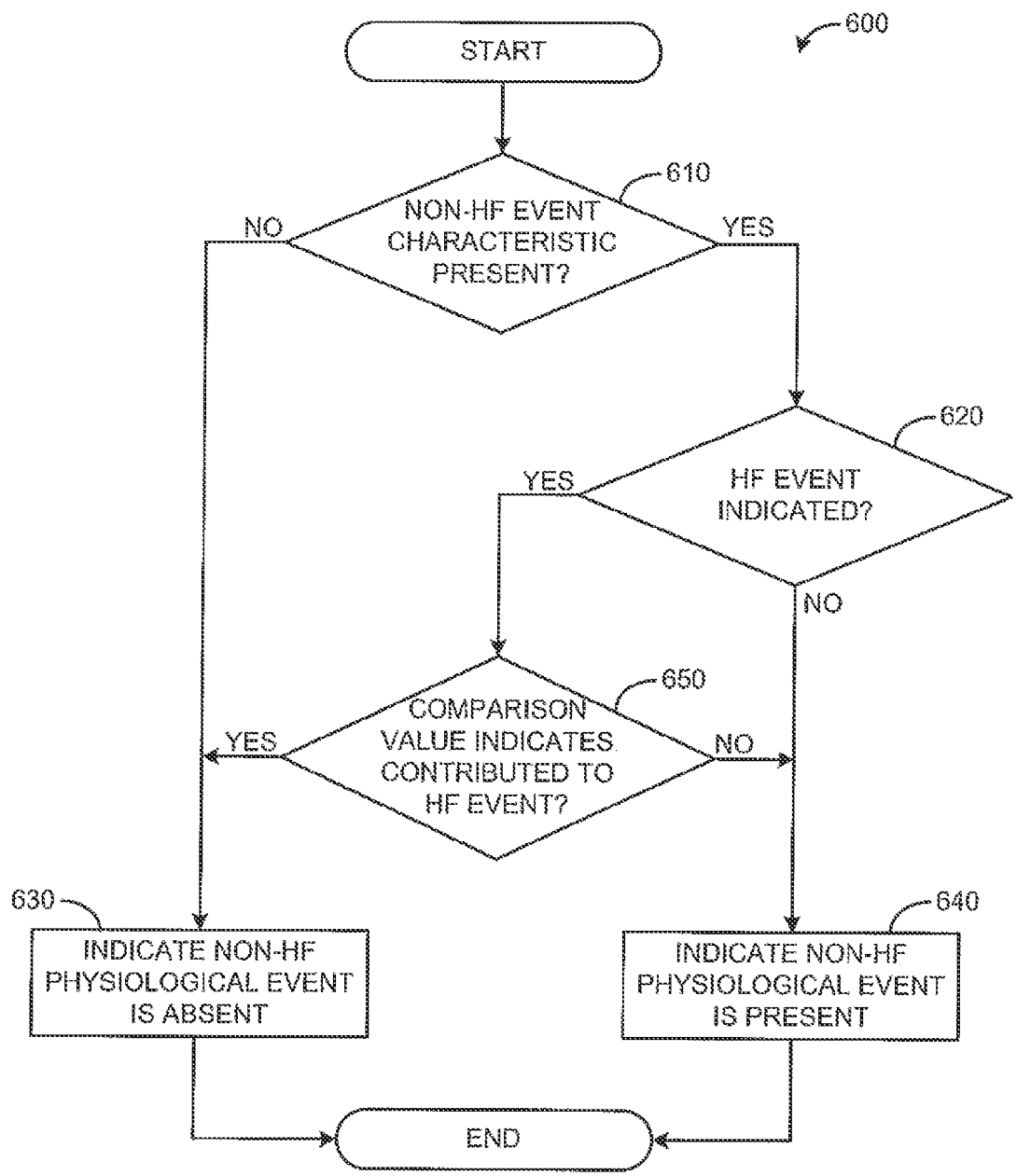
FIG. 6 shows an example of a portion of a method to a non-heart failure physiological event indication of at least one physiological event that did not contribute to an indication of a heart failure event.

FIG. 6 shows an example of a portion of a method 600 to a non-heart failure physiological event indication of at least one physiological event that did not contribute to an indication of a heart failure event. For example, the method 600 can provide an indication of a heart failure event or an indication of a non-heart failure physiological event, such as described at 240 of FIG. 2. In an example, the local monitoring device 105 can be configured, such as by the non-HF status indicator circuit 160, to provide an indication of a non-HF physiological event. At 610, the non-HF status indicator circuit 160 can determine whether a non-HF physiological event characteristic is present, such as determined by the non-HF physiological event detection circuit 150. If a characteristic of a non-HF physiological event is found to be present, the non-HF status indicator circuit 160 can, at 620, determine whether a HF event was indicated, such as by using the HF event indication. Otherwise, at 630, the non-HF status indicator circuit 160 can indicate that a non-HF physiological event is absent and the method ends.

Returning to 620, if a HF event was indicated to be absent, then the non-HF status indicator circuit 160 can, at 650, indicate that a non-HF physiological event is present and the method ends. Otherwise, if the HF event was indicated to be present, the non-HF status indicator circuit 160 can then determine whether the non-HF physiological event characteristic contributed towards the HF event indication, such as using the comparison value determined at 530 by the comparison circuit 155. If so, the non-HF physiological event characteristic indicates that the non-HF event is absent at 620 and the illustrated process exits. Otherwise, the non-HF status indicator circuit can indicate at 640 that the non-HF physiological event is present, and the illustrated process exits.

Figures 7, 8:
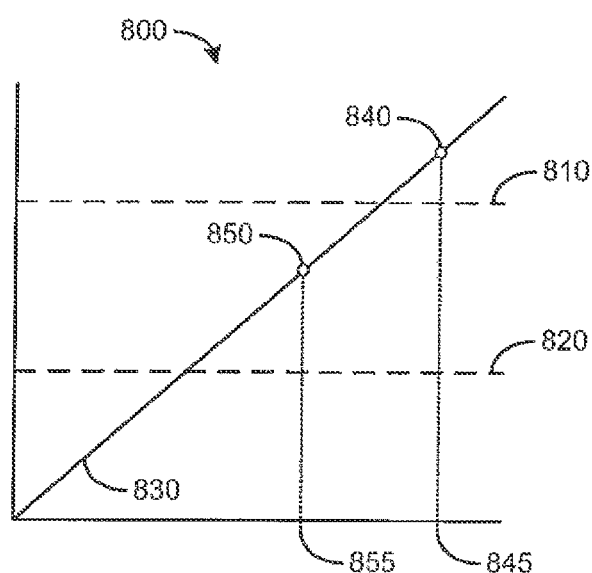
FIG. 7 shows an example of a truth table depicting cases that can generate a non-heart failure physiological event indication of at least one physiological event that did not contribute to an indication of a heart failure event.
FIG. 8 shows an example of a criterion to determine a non-heart failure physiological event indication.

FIG. 7 shows an example of a truth table 700 depicting cases that can generate a non-heart failure physiological event indication of at least one physiological event that did not contribute to an indication of a heart failure event. For example, the truth table 700 shows logical cases in which a non-HF physiological event indication 710 can be indicated as being present (e.g., '1') or absent (e.g., '0'), such as by method 600 using a HF event indication 712, a non-HF physiological event characteristic 714 and a comparison value 716. In an example, a non-HF physiological event indication 710 can be marked as present, such as at 720, when a HF event indication 712 is indicated as being absent and the non-HF physiological event characteristic 714 is present. In such cases, the comparison value 716 does not contribute to the non-HF physiological event indication 710 because no HF event indication 712 was present. In an example, a weight signal can indicate that the subject 170 has experienced a weight loss that exceeds a specified criterion for a time period. In such a case, a HF event detection circuit 145 can be configured to indicate that a HF event is absent when the weight signal indicates a weight loss. However, a non-HF physiological event characteristic can be specified to be present a weight loss exceeds the specified criterion (e.g., a weight loss of at least x pounds within y time period). In such a case, the non-HF physiological event indication can indicate that the weight loss physiological event is present during that time period.

In an example, such as at 730, a non-HF physiological event indication 710 can be indicated as being present when both a HF event indication 712 and a non-HF physiological event characteristic 714 are indicated as being present and the comparison value 714 indicates that the non-HF physiological event characteristic 712 did not contribute to the HF event indication 712. For example, the HF event detection circuit 145 can issue a HF event indication after analyzing signals, such as a respiration rate signal and a thoracic impedance signal, that meet the specified criterion. However, a non-HF physiological event detection circuit 150 can be configured such that a non-HF physiological event characteristic can be declared present when the respiration rate signal and a temperature signal meet one or more specified criteria, individually or in combination, such as to indicate pneumonia. In such a case, the non-HF physiological event characteristic 714 for pneumonia can be declared, e.g., by the comparison circuit 155, to not contribute to the HF event indication 712, so that the non-HF physiological event characteristic 710 can be indicated as present concurrently with the HF event indication 712.

In an example, at 740, a non HF physiological event indication 710 can be indicated as being absent when an indicated non-HF physiological event characteristic 714 is found to contribute to a heart failure event indication 712, such as indicated by a comparison value 716. For example, a HF event detection circuit 145 can indicate that a HF event indication is present using one or more physiological signals, such as using a respiration rate signal. The non-HF physiological event detection circuit 150 can find that a non-HF event characteristic 714 is present, such as indicating dyspnea, using the same respiration rate signal. In such a case, the comparison circuit 155 can compare the respiration rate signal to a criterion, where the criterion indicates that the respiration signal contributed towards the HF event indication 712 issued by the HF event detection circuit 145. Because the respiration rate signal contributed to both the HF event indication 712 and the non-HF physiologic event characteristic 714, the non-HF physiological status indication circuit 160 can indicate that the non-HF physiological event 710 is absent (e.g., masked), such as illustrated at 740.

FIG. 8 shows an example of a criterion 800 to determine a non-heart failure physiological event indication. In an example, the criterion 800 can be used to determine at least one of a HF event indication, a non-HF physiological event characteristic, or a comparison value by a local monitoring device 105. In an example, the criterion 800 can include one or more threshold values 810,820 such as can be compared to a physiological signal received from a sensor 110-120 associated with the subject 170. For example, the threshold values 810,820 can be specified values, or vary as a function of one or more physiological signals. In an example, a HF event detection circuit 145 can indicate that a HF event indication is present, such as when a signal value 830 exceeds the threshold 810. In an example, a non-HF physiological event detection circuit 150 can indicate that a non-HF physiological event characteristic is present, such as when the physiological signal value exceeds a lower threshold value, such as the threshold 820. In an example, the comparison circuit 155 can indicate that the physiological sensor signal contributed to the HF event indication and the non-HF physiological event indication, such as at point 840 at time 845. In an example, the comparison circuit 155 can indicate that the physiological signal 830 did not contribute to a HF event indication, but a non-HF physiological event characteristic can be indicated as being present, such as at point 850 at time 855.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:
1. A system comprising:
a heart failure event detection circuit, configured to analyze information from different physiological signals to determine a heart failure event indication corresponding to a time period;
a non-heart failure physiological event detection circuit, configured to determine a non-heart failure physiological event characteristic including detecting a heart failure co-morbidity different than an improvement or worsening of the heart failure event using at least one of the different physiological signals;

a comparison circuit, configured to compare the at least one of the different physiological signals to a specified criterion indicative of the heart failure event to provide a comparison value indicating whether the non-heart failure physiological event characteristic contributes to the heart failure event indication; and a non-heart failure status indicator circuit, coupled to the heart failure event detection circuit and the non-heart failure physiological event detection circuit and the comparison circuit, and configured to compute a non-heart failure physiological status indication using a logical combination of the heart failure event indication, the non-heart failure physiological event characteristic, and the comparison value; and wherein the non-heart failure physiological status indication indicates that the non-heart failure physiological event is absent, during the time period, when the heart failure event indication indicates that the heart failure event is present during the time period, the non-heart failure event characteristic indicates that the non-heart failure physiological event including the heart failure co-morbidity is present during the time period, and the comparison value indicates that the at least one of the different physiological signals does meet the specified criterion indicative of the heart failure event.

2. The system of claim 1, wherein the non-heart failure physiological status indication indicates that the non-heart failure physiological event is present, during the time period, when the heart failure event indication indicates that the heart failure event is present during the time period, the non-heart failure event characteristic indicates that the non-heart failure physiological event is present during the time period, and the comparison value indicates that at least one of the different physiological signals fails to meet the criterion indicative of the heart failure event.

3. The system of claim 1, wherein the non-heart failure physiological status indication indicates that the non-heart failure physiological event is present, during the time period, when the heart failure event indication indicates that the heart failure event is absent during the time period, the non-heart failure event characteristic indicates that the non-heart failure physiological event is present during the time period, and the comparison value indicates that at least one of the different physiological signals fails to meet the criterion indicative of the heart failure event.

4. The system of claim 1, further comprising one or more physiological sensors configured to provide the at least one of the different physiological signals.

5. The system of claim 4, wherein the at least one of the different physiological signals is selected from a heart rate signal, a respiration signal, a blood pressure signal, a lung tidal volume signal, a physical activity level signal, a weight signal, a posture signal, an impedance signal, a heart sound signal, an airflow or respiration signal, a blood flow signal, a blood pressure signal, a minute ventilation signal, an electrocardiogram, a temperature signal, an autonomic tone signal, an autonomic balance signal, a hematocrit signal, a cardiac muscle contractility signal, an oxygen saturation level signal, a blood analyte signal, or a myocardial ischemia signal.

6. The system of claim 4, wherein the physiological sensor is configured to provide a respiration signal.

7. The system of claim 4, wherein the at least one of the different physiological signals comprises two or more physiological signals, wherein the criterion indicative of the heart failure event comprises a threshold, wherein the threshold corresponds to an interaction characteristic of said two or more physiological signals.

8. The system of claim 7, wherein a first of said two or more physiological signals is a respiration rate having a high respiration rate characteristic, and a second of said two or more physiological signals is a weight signal having a weight gain characteristic.

9. The system of claim 1, wherein the specified criterion indicative of the heart failure event is a threshold.

10. The system of claim 1, wherein the specified criterion indicative of the heart failure event is a weighting factor, wherein the weighting factor corresponds to an interaction characteristic of the two or more physiological signals.

11. The system of claim 1, comprising a remote monitoring system communicatively coupled to the heart failure event detection circuit and the non-heart failure status indicator circuit, wherein the remote monitoring system is configured to provide the heart failure event indication and the non-heart failure physiological status indication to a user.

12. The system of claim 11, wherein the remote monitoring system is configured to provide the heart failure event indication and the non-heart failure physiological status indication to a user through a graphical user interface.

13. The system of claim 1, wherein the heart failure event indication is a binary value.

14. The system of claim 1, wherein the heart failure event indication comprises a heart failure event status indication and physiological sensor signal information.

15. The system of claim 1, wherein the non-heart failure physiological status indication comprises a non-heart failure event status indication and physiological sensor signal information.

16. A method comprising:

analyzing information from different physiological signals by a heart failure event detection circuit to determine a heart failure event indication corresponding to a time period;

determining a non-heart failure physiological event characteristic including detecting a heart failure co-morbidity different than an improvement or worsening of the heart failure event by a non-heart failure physiological event detection circuit using at least one of the different physiological signals;

comparing, using a comparison circuit, the at least one of the different physiological signals to a specified criterion indicative of the heart failure event to provide a comparison value indicating whether the non-heart failure physiological event characteristic contributes to the heart failure event indication; and computing, using a non-heart failure status indicator circuit, a non-heart failure physiological event indication using a logical combination of the heart failure event indication, the non-heart failure physiological event characteristic, and the comparison value; and wherein the non-heart failure physiological status indication indicates that the non-heart failure physiological event is absent, during the time period, when the heart failure event indication indicates that the heart failure event is present during the time period, the non-heart failure event characteristic indicates that the non-heart failure physiological event including the heart failure co-morbidity is present during the time period, and the comparison value indicates that the at least one of the different physiological signals does meet the specified criterion indicative of the heart failure event.

17. The method of claim 16, wherein the non-heart failure physiological status indication indicates that the non-heart failure physiological event is present, during the time period, when the heart failure event indication indicates that the heart failure event is present during the time period, the non-heart failure event characteristic indicates that the non-heart failure physiological event is present during the time period, and the comparison value indicates that the at least one of the different physiological signals fails to meet the criterion indicative of the heart failure event.

18. The method of claim 16, wherein the non-heart failure physiological status indication indicates that the non-heart failure physiological event is present, during the time period, when the heart failure event indication indicates that the heart failure event is absent during the time period, the non-heart failure event characteristic indicates that the non-heart failure physiological event is present during the time period, and the comparison value indicates that the at least one of the different physiological signals fails to meet the criterion indicative of the heart failure event.

19. The method of claim 16, further comprising receiving the at least one of the different physiological signals.

20. The method of claim 19, wherein the at least one of the different physiological signals is selected from one of a heart rate signal, a respiration signal, a blood pressure signal, a lung tidal volume signal, a physical activity level signal, a weight signal, a posture signal, an impedance signal, a heart sound signal, an airflow or respiration signal, a blood flow signal, a blood pressure signal, a minute ventilation signal, an electrocardiogram, a temperature signal, an autonomic tone signal, an autonomic balance signal, a hematocrit signal, a cardiac muscle contractility signal, an oxygen saturation level signal, a blood analyte signal, or a myocardial ischemia signal.

\* \* \* \* \*